United States Patent
Gupta et al.

(10) Patent No.: US 10,813,744 B2
(45) Date of Patent: Oct. 27, 2020

(54) RECHARGEABLE INTRAOCULAR IMPLANT

(71) Applicants: Elenza, Inc.; Greatbatch Ltd., Clarence, NY (US)

(72) Inventors: Amitava Gupta, Roanoke, VA (US); Rudy Mazzocchi, Coral Springs, FL (US); Roel Trip, Valencia, CA (US); Brian Peterson, East Aurora, NY (US); George Cintra, Jamestown, RI (US); Joey Chen, Stevenson Ranch, CA (US); Leslie Halberg, Valencia, CA (US)

(73) Assignees: Greatbatch Ltd., Clarence, NY (US); Elenza, Inc., Roanoke, VA (US)

( * ) Notice: Subject to any disclaimer, the term of this patent is extended or adjusted under 35 U.S.C. 154(b) by 12 days.

(21) Appl. No.: 15/757,315

(22) PCT Filed: Sep. 3, 2015

(86) PCT No.: PCT/US2015/048334
§ 371 (c)(1),
(2) Date: Mar. 2, 2018

(87) PCT Pub. No.: WO2017/039672
PCT Pub. Date: Mar. 9, 2017

(65) Prior Publication Data
US 2018/0243083 A1    Aug. 30, 2018

(51) Int. Cl.
*A61F 2/16* (2006.01)
*H02J 50/12* (2016.01)
(Continued)

(52) U.S. Cl.
CPC ............ *A61F 2/1624* (2013.01); *H02J 7/025* (2013.01); *H02J 50/70* (2016.02); *H02J 50/80* (2016.02);
(Continued)

(58) Field of Classification Search
None
See application file for complete search history.

(56) References Cited

U.S. PATENT DOCUMENTS

| | | |
|---|---|---|
| 2,311,796 A | 2/1943 | Wrathall |
| 4,300,818 A | 11/1981 | Schachar |
| (Continued) | | |

FOREIGN PATENT DOCUMENTS

| | | |
|---|---|---|
| AU | 2014227430 A1 | 4/2015 |
| JP | 2013-156632 A | 8/2013 |
| (Continued) | | |

OTHER PUBLICATIONS

International Search Report received in PCT/US2015/048334, dated Dec. 2, 2015.
(Continued)

*Primary Examiner* — Leslie Lopez
(74) *Attorney, Agent, or Firm* — Michael F. Scalise

(57) ABSTRACT

An intraocular implant (IOI) includes a lens structure with variable optical power, a sensor that detects an optical accommodation response, a rechargeable power storage device, a recharging interface, a wireless communication interface, and a controller. The controller can receive information from the sensor indicating an optical accommodation response, control the lens structure to vary the variable optical power based on the information received from the sensor, control the recharging interface to recharge the rechargeable power storage device, and further control the recharging interface to receive power for operation of the IOI, and transmit and receive information through the wireless communication interface.

22 Claims, 11 Drawing Sheets

(51) Int. Cl.
*H02J 7/02* (2016.01)
*H02J 50/70* (2016.01)
*H02J 50/80* (2016.01)
*G02C 11/00* (2006.01)
*A61F 9/007* (2006.01)
*H01F 38/14* (2006.01)
*H02J 7/34* (2006.01)
*H02J 7/35* (2006.01)

(52) U.S. Cl.
CPC ... *A61F 9/00781* (2013.01); *A61F 2250/0002* (2013.01); *G02C 11/10* (2013.01); *H01F 38/14* (2013.01); *H02J 7/345* (2013.01); *H02J 7/35* (2013.01); *H02J 50/12* (2016.02)

(56) References Cited

U.S. PATENT DOCUMENTS

| | | | |
|---|---|---|---|
| 4,309,603 A | 1/1982 | Stauffer | |
| 4,373,218 A | 2/1983 | Schachar | |
| 4,466,703 A | 8/1984 | Nishimoto | |
| 4,601,545 A | 7/1986 | Kern | |
| 4,770,494 A | 9/1988 | Csencsits et al. | |
| 4,787,903 A | 11/1988 | Grendahl | |
| 5,066,301 A | 11/1991 | Wiley | |
| 5,653,751 A | 8/1997 | Samiy et al. | |
| 6,200,342 B1 | 3/2001 | Tassignon | |
| 6,282,449 B1 | 8/2001 | Kamerling et al. | |
| 6,619,799 B1 | 9/2003 | Blum et al. | |
| 6,638,304 B2 | 10/2003 | Azar | |
| 6,706,066 B1 | 3/2004 | Zhou et al. | |
| 6,790,232 B1 | 9/2004 | Lang | |
| 7,041,133 B1 | 5/2006 | Azar | |
| 7,480,980 B2 | 1/2009 | Jung et al. | |
| 7,926,940 B2 | 4/2011 | Blum et al. | |
| 7,964,833 B2 | 6/2011 | Holladay | |
| 9,070,507 B2 | 6/2015 | Dronov et al. | |
| 2006/0095128 A1 | 5/2006 | Blum et al. | |
| 2009/0033863 A1 | 2/2009 | Blum et al. | |
| 2009/0264966 A1* | 10/2009 | Blum | A61N 1/36046 607/61 |
| 2013/0194540 A1* | 8/2013 | Pugh et al. | G02C 7/02 351/159.03 |
| 2013/0238090 A1* | 9/2013 | Pugh et al. | A61F 2/1624 623/6.13 |
| 2014/0058506 A1* | 2/2014 | Tai et al. | A61F 2/14 623/4.1 |
| 2014/0148899 A1* | 5/2014 | Fehr | A61F 2/1624 623/6.22 |

FOREIGN PATENT DOCUMENTS

| | | |
|---|---|---|
| JP | 2014-533969 A | 12/2014 |
| JP | 2015-062063 A | 4/2015 |
| WO | WO-2007/047111 A1 | 4/2007 |
| WO | WO-2012/120412 A1 | 9/2012 |
| WO | WO-2013/033349 A1 | 3/2013 |
| WO | WO-2013/081773 A1 | 6/2013 |
| WO | WO-2015/031241 A1 | 3/2015 |

OTHER PUBLICATIONS

Written Opinion of the International Searching Authority received in PCT/US2015/048334, dated Dec. 2, 2015.
International Preliminary Report on Patentability received in corresponding International application PCT/US2015/048334 dated Mar. 15, 2018, 8 pages.

* cited by examiner

RECHARGEABLE INTRAOCULAR IMPLANT

CROSS-REFERENCE TO RELATED APPLICATIONS

The present application is the U.S. National Stage of International Application PCT/US2015/048334, filed Sep. 3, 2015, the entire disclosure of which is incorporated herein by reference.

BACKGROUND

Intraocular implants (IOIs) may include a power supply among other components. It is desirable to reduce the size of an IOI while maintaining functionality. Reduction of the size of the power supply is correspondingly desirable.

SUMMARY

The present disclosure describes an IOI with reduced size.

In an embodiment, an IOI includes a lens structure with variable optical power, a sensor that detects an optical accommodation response, a rechargeable power storage device, a recharging interface, a wireless communication interface, and a controller. The controller can receive information from the sensor indicating an optical accommodation response, control the lens structure to vary the variable optical power based on the information received from the sensor, control the recharging interface to recharge the rechargeable power storage device, and further control the recharging interface to receive power for operation of the IOI, and transmit and receive information through the wireless communication interface.

In an embodiment, an IOI includes an electromagnetic recharging interface, where the recharging interface is a radiofrequency (RF) interface including a resonant circuit, and the resonant circuit includes a coil. The IOI further includes an energy storage device and a controller. The controller controls the RF interface to recharge the energy storage device, and communicates through the RF interface, including providing an indication externally that a recharge is needed.

In an embodiment, an IOI includes an electromagnetic recharging interface, where the recharging interface includes a photovoltaic device that converts electromagnetic energy into electrical energy. The IOI further includes an energy storage device and a controller. The controller controls the recharging interface to recharge the energy storage device, and communicates through the recharging interface, including providing an indication externally that a recharge is needed.

BRIEF DESCRIPTION OF THE DRAWINGS

FIG. 5A illustrates a coil in recharging interface, and FIG. 5B illustrates a coil in a recharger.

DETAILED DESCRIPTION

Figure 1:
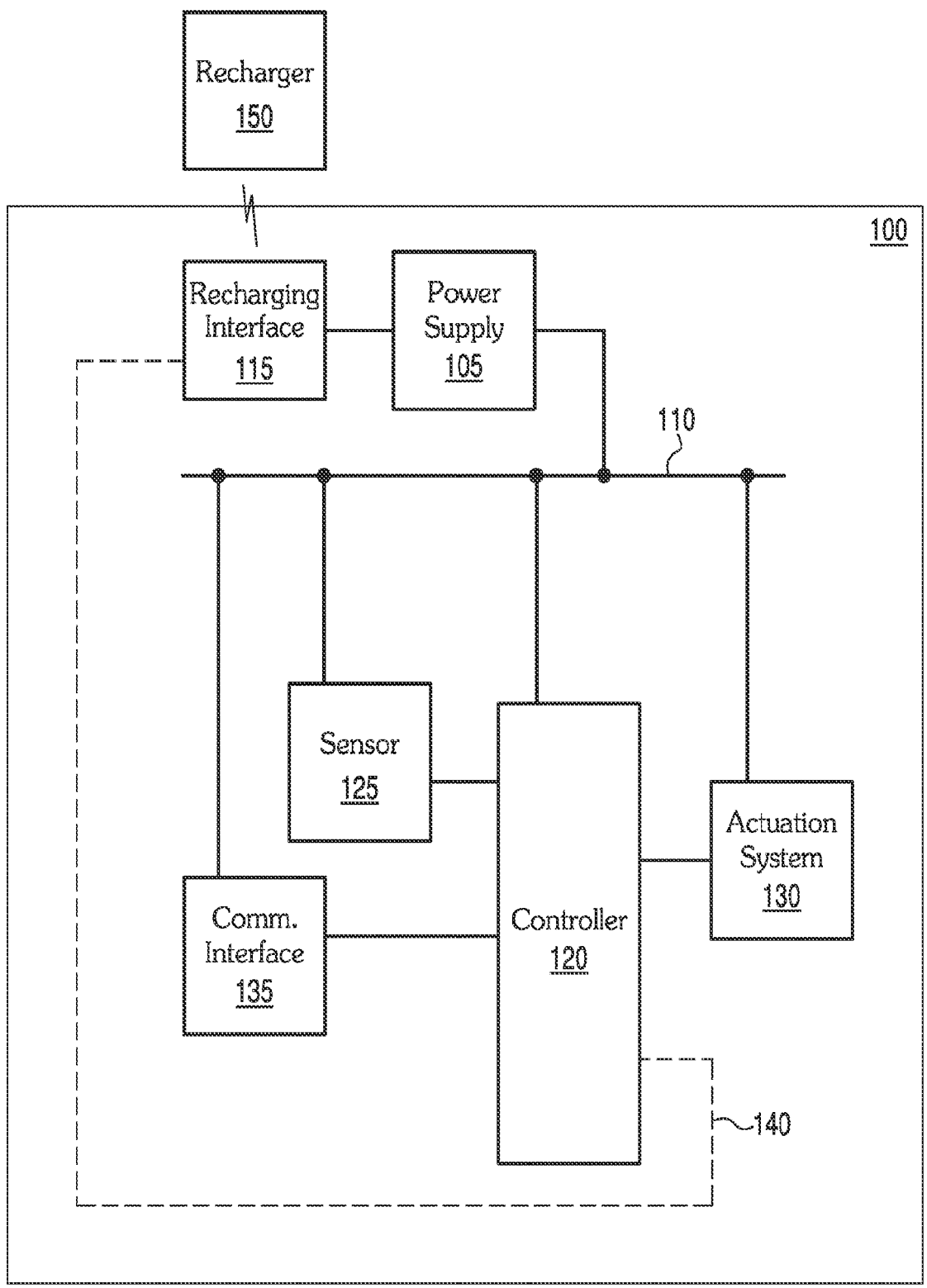
FIG. 1 illustrates an example of an IOI in accordance with an embodiment of the present disclosure.

An IOI may include an actuation system to provide dynamic or switchable functionality, where the actuation system is controlled by a controller based on information from in-situ sensors coupled to the controller. For example, a sensor may detect a physiological change indicating that a person in whom the IOI is implanted wished to change focus, and the controller may control the actuation system to change the focus. For another example, a flow sensor in the anterior chamber of the eye of a person with glaucoma may detect a reduced flow of aqueous, signaling that the intraocular pressure (IOP) is rising and therefore an adjustment of an opening of a shunt or valve is needed to increase aqueous outflow and thereby reduce the IOP, which can damage the optic nerve.

Because one or more of the controller, the actuation system, and the sensors may operate using electrical power, an IOI may include a power supply to provide power to components within the IOI. It is desirable to reduce the size of an IOI to minimize invasiveness and to optimize options for surgical techniques and device placement, while maintaining functionality. Reduction of the power supply size is correspondingly desirable.

An IOI power supply according to one or more embodiments of the present disclosure draws operating power from one or more internal rechargeable energy sources. An internal energy source is recharged through a recharging interface from external energy sources. Recharging is controlled by the power supply, by a controller in the IOI, by an external recharger, or by a combination thereof. In one or more embodiments, the power supply may additionally draw operating power through one or more recharging interfaces from external energy sources.

Utilization by the power supply of more than one energy source within the IOI or external to the IOI is desirable, to optimize usability, maximize run time, and take advantage of available sources of energy. Some sources of energy are made available in a custom form, whereas others are standard, ubiquitous, or made available naturally. Custom and standard sources of energy include batteries, cells, and other energy storage devices, and wired or wireless recharging devices. Ubiquitous sources of energy include, for example, artificial lighting, ambient radiofrequency energy, and ambient energy within other frequency ranges. Natural sources of energy include sunlight, chemicals within the body, relative motion, and muscle movement, among others.

In one or more embodiments, the power supply is capable of switching between rechargeable sources of energy, between recharging interfaces, or between a rechargeable source of energy and a recharging interface. Such switching may be performed seamlessly, so as to avoid wearer-noticeable change in IOI function do to the switching. Further, an internal energy source may receive energy through a recharging interface while the power supply is drawing energy from an internal energy source, and internal energy sources may receive energy through multiple recharging interfaces concurrently.

In one or more embodiments, the IOI detects availability of an energy source, and initiates recharging from the energy source through a recharging interface. The initiation of recharging instance may occur whether or not the energy source to be recharged has reached a discharge threshold, such as a threshold used to initiate a request for recharging.

Recharging may be performed, for example, through inductive charging using an external unit that provides energy to the IOI. Batteries and cells may be large relative to the dimensions of the eye, may be associated with increased risk of leakage or other failure, and replacement requires surgery. There is a continuing desire for improvements in the power system of an IOI, such as improvements in size, reliability, and capability. The present disclosure describes an improved IOI with an improved power system.

FIG. 1 illustrates an example of an IOI 100 in accordance with an embodiment of the present disclosure. The IOI 100 includes a power supply 105, a power bus 110, a recharging interface 115, a controller 120, one or more sensors 125, an actuation system 130, and a communication interface 135. The IOI 100 may have additional or fewer components, or multiple of the same component.

The power supply 105, described below, provides power to the power bus 110. In one or more embodiments, the power bus 110 includes a single power line (such as a wire or a trace); in other embodiments, the power bus 110 includes multiple power lines. In embodiments in which the power bus 110 includes multiple power lines, the power provided on each power line may be the same or different. For example, one power line may provide a low voltage and low current to the controller 120, whereas another power line may provide a low voltage and higher current to the actuation system 130.

The power supply 105 includes one or more energy sources that are rechargeable through a recharging interface 115, described below.

The controller 120 receives power from the power bus 110, receives sensor data from the sensor 125, controls the actuation system 130, and communicates externally by way of the communication interface 135.

Examples of a controller 120 used in an IOI include a logic controller, an application-specific integrated circuit (ASIC), a field-programmable gate array (FPGA), a microprocessor, a microcontroller, other circuitry effecting processor functionality, or a combination thereof, along with associated logic and interface circuitry. The controller executes instructions, which may be implemented in hardware, firmware or software. For software-implemented instructions and some firmware-implemented instructions, the instructions are stored in a memory device, which may be external to the controller or integrated into the controller. The memory device may be one or both of volatile and non-volatile memory for storing information (e.g., instructions and data). Examples of a memory device include a semiconductor memory device such as an EPROM, an EEPROM, a flash memory, a RAM, or a ROM device.

An advantage of hardware-implemented instructions is that the memory or the controller may be implemented in a smaller sized package; an advantage of firmware or software instructions is that they may be reprogrammed, such as to add new functionality, modify existing functionality, turn off existing functionality, and download data. For example, a data download may include modifications of settings for focal length in different switched states as a patient ages, or may include a record of adjustments or operations performed that would affect the behavior of the IOI. For another example, a physician may determine that a particular feature is to be turned off when a condition of a patient's eye changes, or that the IOI be shut off before an operation.

An embodiment of the disclosure relates to a non-transitory computer-readable storage medium (e.g., a memory device as described above) having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel, and further transferred to the IOI.

Communication interface 135 represents electrical components and optional code that together provide a wireless interface to external devices. Communication interface 135 may be bi-directional, such that, for example, data may be sent from the controller 120, and instructions and updates may be received by the controller 120.

External to the IOI 100 is a wireless recharger 150, described below, that provides energy to the recharging interface 115 to recharge the power supply 105.

In one or more embodiments, the IOI 100 incorporates a power management scheme to reduce instantaneous and/or overall power draw. In one or more embodiments, the controller 120 controls the power supply 105 to switch off one or more outputs to the power bus 110, thereby removing power from one or more components of the IOI 100. For example, if no accommodative magnification is presently needed in an accommodative IOI 100, power to the actuation system 130 may be removed, and magnification allowed to return to a default state. In one or more embodiments, the power supply 105 additionally or alternatively controls one or more power states of the IOI 100, such as providing a signal to the controller 120 to move to a lower-power state, or providing a signal to the communication interface to wake up from a lower power state. In one or more embodiments, the controller 120 is able to transition itself between two or more power states.

In one or more embodiments, the controller 120 monitors the environment to identify when a suitable external energy source is available for recharging, and initiates recharging based on the availability of the external energy source. Such an initiation of recharging may be performed when a parameter of an internal energy source (e.g., a voltage or current level, or an indicator provided by the internal energy source) indicates that the internal energy source is at or close to a discharge threshold. However, an initiation of recharging may be performed if the internal energy source has capacity for additional energy, whether or not the parameter indicates a present or near discharge condition. Further, if the controller 120 identifies a suitable available external energy source, the controller 120 may direct the power supply to draw power from the external energy source alternatively or additionally to the internal energy source.

In one or more embodiments, the controller 120 monitors an indicator of the power supply 105 to determine when recharging of an internal energy source is needed. In one or more embodiments, the controller 120 provides a signal requesting recharging, such a signal 140 to the recharging interface 115 to connect to the power supply 105 and prepare for recharging, or a signal sent through the communication interface 135 to notify the person in which the IOI 100 is implanted that it is time to recharge. Such a signal through the communication interface 135 may be sent, for example, to the recharger 150, to a wearable notification device, or to a mobile device such as a smart phone or tablet computer, to initiate an audio or visual notification (e.g., a sound, a light, a text, an icon, an email, and so forth). In one or more embodiments, if the controller 120 identifies a need for recharging, the controller 120 may control the power supply or other components of the IOI to operate at a reduced power draw state.

The controller 120 may provide notifications through the communication interface 135 that attention is needed with respect to other aspects of the IOI 100, such as that data buffers are full of data to be uploaded, or that parameters detected by the sensor 125 have crossed a threshold, or such as that a portion of, or all of, the IOI 100 is malfunctioning, is shutting down, or needs shutting down by way of an external action.

The communication interface 135 may also be used, for example, during manufacturing (e.g., for communication with a post-assembly test system), or during a visit with a physician (e.g., for communication with a test or reprogramming device). Further, a person may use a remote control device for access through the communication interface 135, such as to shut off the IOI 100 during sleep, or to adjust a focal power of the IOI 100.

In one or more embodiments, the sensor 125 detects a physiological response that occurs when a person tries to change focus and experiences an accommodative impulse. An example of a sensor 125 that detects a physiological response is a photosensor. For example, one or more photosensors are positioned at points on the anterior surface of a lens in the IOI. Signals from the photosensors are filtered and interpreted by the controller 120, to determine when changes in signal amplitude represent pupillary constriction caused by an accommodative impulse. For another example, the sensor 125 may be an electrochemical sensor that senses chemical changes in the eye before accommodation begins. For a further example, the sensor 125 may be a pressure sensor. Other types of sensors 125 may alternatively or additionally be used. In one or more embodiments, the sensor 125 is multiple types of sensors 125, such as a combination of two or more of photosensors, electrochemical sensors, pressure sensors, or other sensors.

The actuation system 130 is controlled by the controller 130 to change the focus of the optics in the IOI. An example of an actuation system 130 includes two or more actuators that compress a perimeter of a lens (either along the focal path, or at an angle with respect to the focal path) to change a shape of the lens. Another example of an actuation system 130 is a circuit that provides a voltage to a material, such as a liquid crystal, to change its density and thereby change a focus of a lens incorporating the liquid crystal. Another example of an actuation system 130 is a structure that changes shape when heated, so as to move two lenses towards or away from each other. Other actuation systems 130 may be used. Different type of actuation may be used in combination.

The power supply 105 includes logic and circuitry for delivery of power throughout the IOI 100. The power supply 105 may be, or may include, an IC or an ASIC, and may include switches for engaging/disengaging power to portions of the IOI, such as for implementing an energy saving policy.

Figure 2:
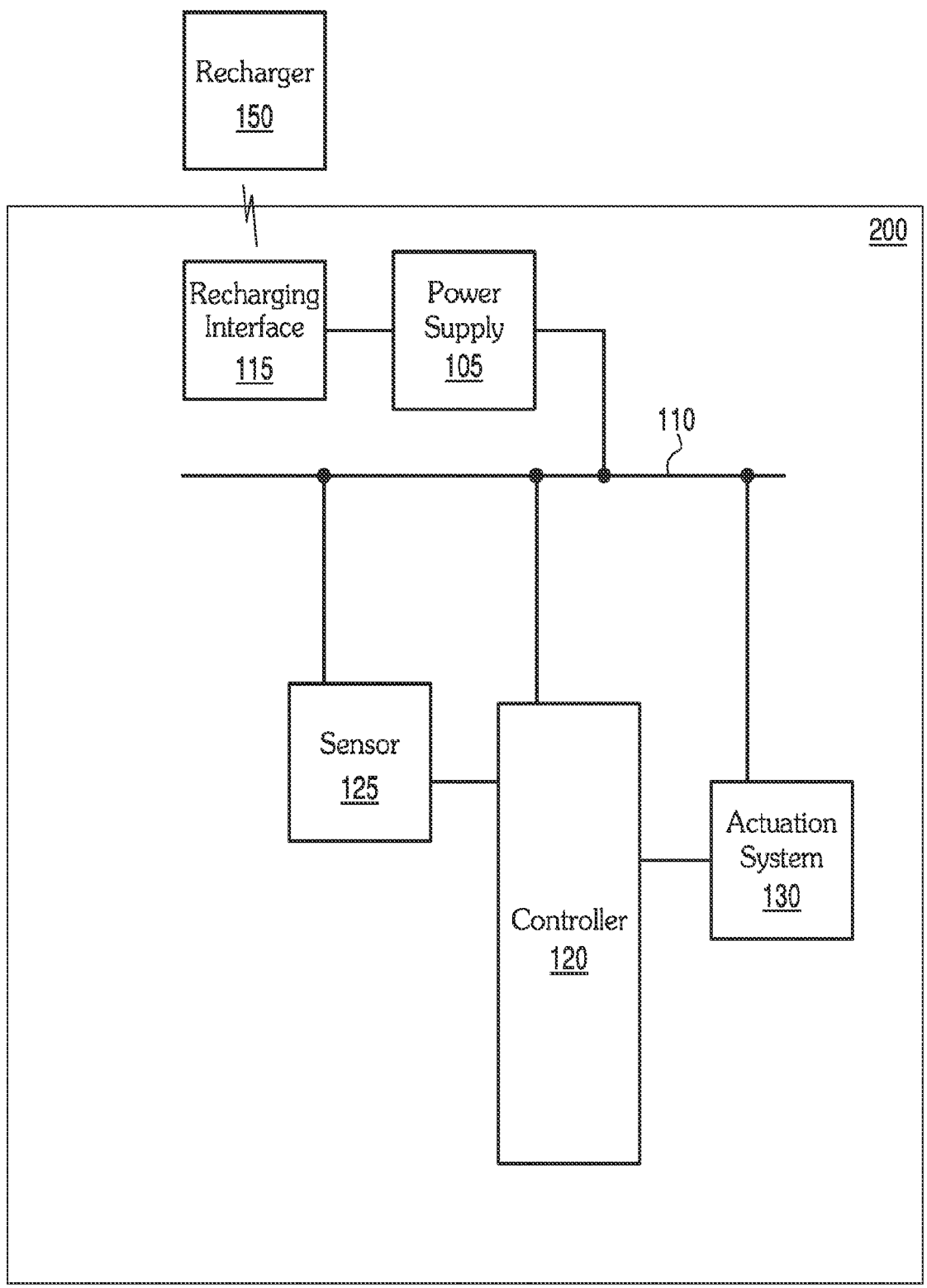
FIG. 2 illustrates an example of an IOI in accordance with an embodiment of the present disclosure.

FIG. 2 illustrates an IOI 200 according to an embodiment of the present disclosure that is similar to the embodiment of FIG. 1, except that the recharging interface 115 and the communication interface 135 of FIG. 1 are combined into one recharging interface 115 with the capability for communication, and the wireless recharger 150 (or one or more of multiple available wireless rechargers 150) may include a corresponding capability for communication. Because the recharging interface 115 of FIG. 2 also includes a capability for communication, there may be configuration differences between the recharging interface 115 of FIG. 1 and the recharging interface 115 of FIG. 2.

In one or more embodiments (such as the embodiments of FIGS. 1 and 2), the IOI (e.g., IOI 100 or 200) is capable of receiving of energy through a recharging interface and substantially concurrently receiving or transmitting data or other communications. For example, substantially concurrent receiving of energy and receiving or transmitting data or other communications can occur simultaneously, in a time sliced sequence or other sequence.

Having described an IOI 100 and an IOI 200 generally, more detail is next provided with respect to the recharging interface 115.

Figure 3A:
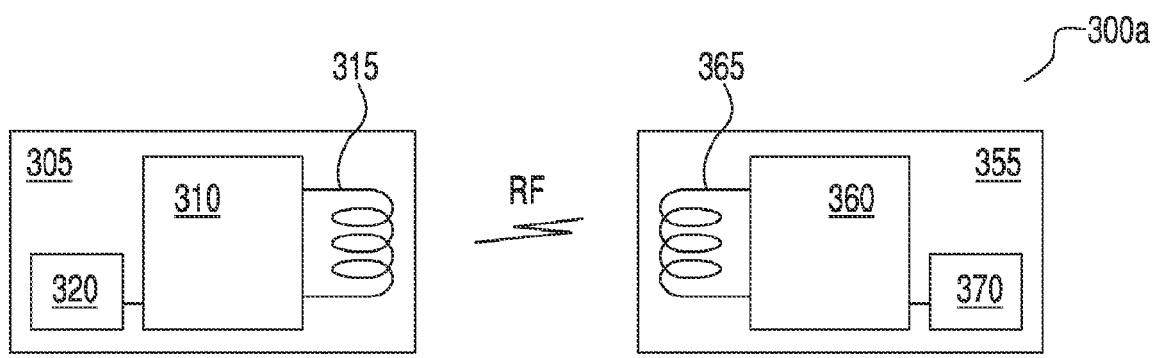
FIG. 3A illustrates an example of a radiofrequency (RF) recharging system in accordance with an embodiment of the present disclosure.

FIG. 3A illustrates an example of an RF inductive coupling recharging system 300a including a recharging interface 305 in an IOI and a recharger 355 external to the IOI. The recharging interface 305 includes circuitry 310 coupled to a coil 315 and an energy storage component 320. The recharger 355 includes circuitry 360 coupled to a coil 365 and an energy storage component 370. The circuitry 310, 360 includes passive electronic components, such as resistors, capacitors, inductors, which may be individual components, or one or more of the components may be integrated together.

The energy storage component 320 is small, to reduce the size of the IOI. In one or more embodiments, the energy storage component 320 is a rechargeable battery or a micro-fuel cell. In one or more embodiments, the energy storage component 320 is a super-capacitor or ultra-capacitor. Although a super-capacitor may have less energy storage capacity than a rechargeable battery or a micro-fuel cell, the super-capacitor may not only be smaller, but may also be more stable. Additionally, the use of super-capacitors may provide for improved reliability of the IOI, because, for example, super-capacitors may have a cycle life of several hundred thousand to a million cycles, whereas batteries may have a cycle life of less than 10,000 cycles.

In context, an IOI may draw 120 microwatt hours (μWh) of electrical energy per day of operation. A typical rechargeable lithium polymer or lithium ion battery may provide about 100 Watt hours per kilogram (Wh/kg) of energy density, which translates to about 7 milligrams (mg) of active material to allow recharging of the IOI to take place about once a week. Limitations of an IOI allow, for example, a weight of preferably less than 15 mg. Thus, for example, if the weight of the power supply casing, electrical leads and feed-throughs is approximately 10 mg, the active material of the battery should have a weight of less than 5 mg.

With respect to an ultra-capacitor, a typical ultra-capacitor has an energy density of about 4.5 Wh/kg. Thus, recharging for an active material weighing about 5 mg would be needed about 6 times per day.

Although more frequent recharging is needed for a super-capacitor or ultra-capacitor, the advantages of the corresponding long life, stability, and small size for the IOI are desirable features.

Accordingly, the recharger 355 of FIG. 3A is physically small, so that it may be unobtrusively attached to a wearable item for supplying recharging energy throughout the day. For example, the recharger 355 may be attached to glasses or other wearable item, or may be attached to or included within a device that is commonly used by the person throughout the day, such as a mobile phone or laptop computer. A person may have several rechargers 355 available. In one or more embodiments, to further reduce a physical size of the recharger 355, the recharger 355 is a repeater, which wirelessly receives energy from another device and wirelessly provides energy to the recharging interface 305.

Figure 3B:
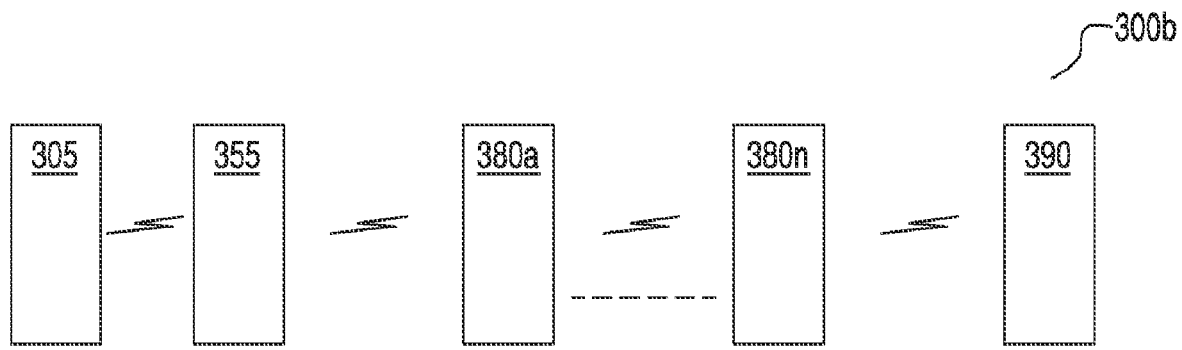
FIG. 3B illustrates an example of a RF recharging system in accordance with an embodiment of the present disclosure.

FIG. 3B illustrates a system 300b including a recharging interface 305 and a recharger 355 as described with respect to FIG. 3A, and further including repeaters 380a-380n and a main recharging unit 390. The storage capacity of the energy storage component 370 of the recharger 355 may be significantly reduced in the system embodiment of FIG. 3B versus the system embodiment of FIG. 3A. For example, in one or more embodiments, the recharger 355 receives small amounts of energy in each energy transfer from the repeater 380a, and delivers energy to the recharging interface 305 in small amounts, so that a complete recharging of the energy storage component 320 includes a sequence alternating between energy transfers from the repeater 380a to the recharger 355 and energy transfers from the recharger 355 to the recharging interface 305. For another example, in one or more embodiments, the energy storage component 370 is sized to store energy sufficient to perform a complete recharging of the energy storage component 320, and receives energy transfers from the repeater 380a after the energy storage component 320 has been recharged. In other embodiments, the energy storage component 370 is sized to store energy sufficient to perform multiple recharges of the energy storage component 320.

Repeater 380a is similarly recharged from a repeater 380(a+1), which is recharged from a repeater 380(a+2) and so forth. The repeater 380n, which is the repeater 380 presently positioned closest to the main recharging unit 390, is recharged from the main recharging unit 390. For example, the main recharging unit 390 may be connected to a house main or may include a large battery, such that energy is available in an effectively unlimited manner. The main recharging unit 390 transfers energy to the repeater 380n, which transfers energy through the repeaters 380 to the repeater 380a, which transfers energy to the recharger 355, which transfers energy to the recharging interface 305. It should be noted that the repeaters 380 may be one repeater 380, which receives energy from the main recharging unit 390 and transfers energy to the recharger 355. Energy may be transferred in approximately the same amount in each energy transfer, or in different amounts. Further, the energy storage capacity and energy transfer capability of one or more of the recharger 355 and repeater(s) 380 may be different. By way of example, the repeater 380n may have storage capacity significantly greater than the other repeaters 380, and may receive an amount of energy in a transfer that is magnitudes greater than an amount of energy transferred to a repeater 380(n-1) in a transfer. In another example, each repeater 380 receives a transfer of energy sufficient to charge the next device in line, whether the next device in line is another repeater 380 or the recharger 355. In one or more embodiments, energy is transferred in a just-in-time manner. In other words, for example, the recharging interface 305 notifies the recharger 355 that a recharging is needed or is about to begin, and the notification is sent through the repeaters 380 to the main recharging unit 390 to begin an energy transfer. The energy transfer may be performed in a sequence of small transfers to the repeater 380n, which propagates each small transfer down the line as it is received. Using such a technique, each of the repeaters 380 and the recharger 355 may be small-form devices so as to be unobtrusive, and the recharging interface 305 may be small in form to reduce the size of the IOI.

The repeaters 380 may be placed throughout a room or a vehicle, or throughout rooms of a building, such that they may be inconspicuously positioned to provide energy to the recharger 355 throughout the day. When a subject with an IOI leaves the vehicle or building, a mobile main recharging unit 390 may be carried along, such as carrying a battery power pack in a purse. Additionally, the recharger 355 may be positioned in a pillow, a sleeping mask, or other night-use object, for convenience of the subject.

Figure 4:
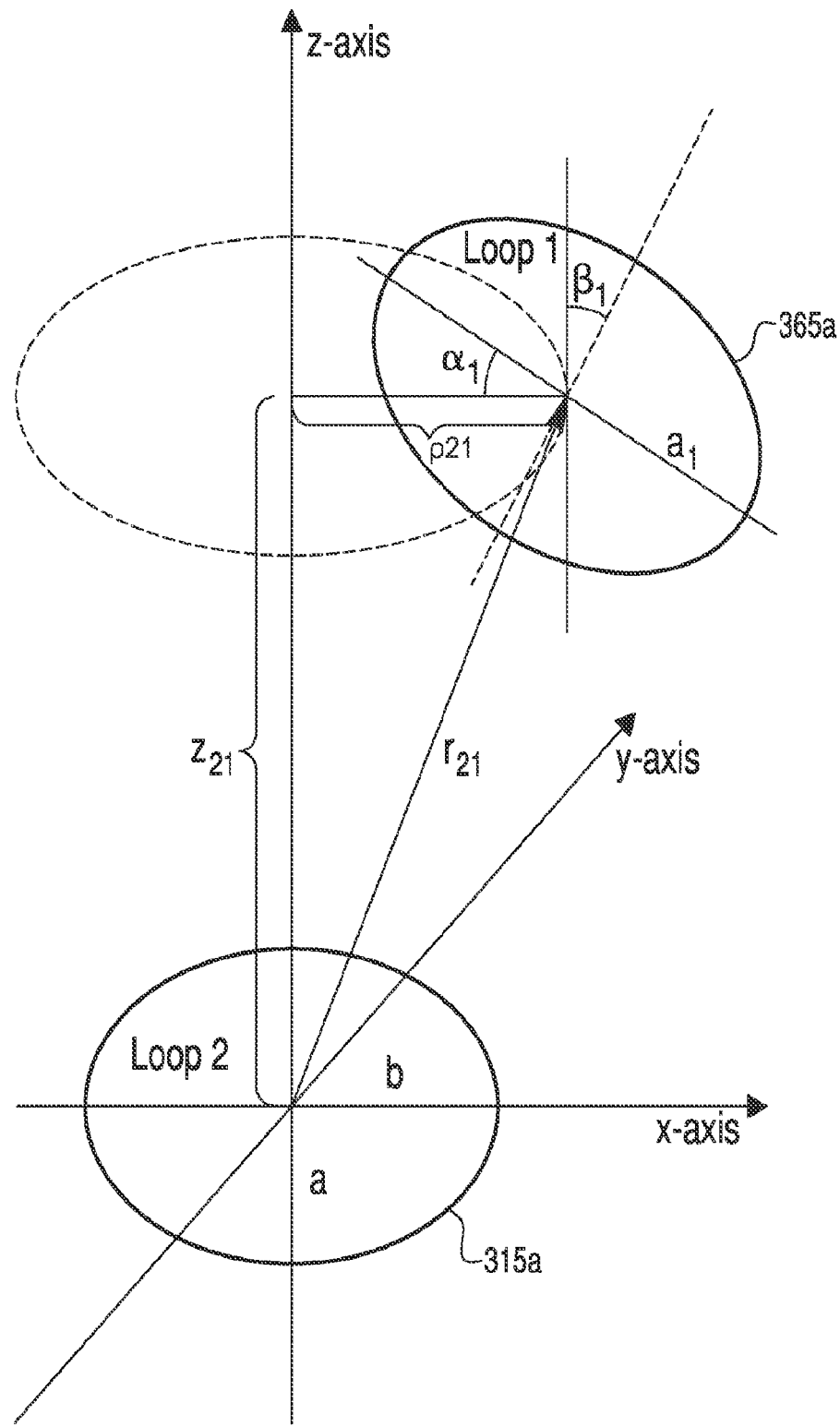
FIG. 4 illustrates an example of a pair of coils in an RF recharging system in accordance with an embodiment of the present disclosure.

FIG. 4 illustrates a pair of coils in an RF recharging system in accordance with an embodiment of the present disclosure, including a coil 315a ("Loop 2", an example of the coil 315 of the recharging interface 305), and a coil 365a ("Loop 1", and example of the coil 365 of the recharger 355) positioned with respect to each other for a transfer of energy.

Table 1 provides parameters of an example of an RF link coupling corresponding to the embodiment of FIG. 4 ('mm' refers to millimeters; 'deg' refers to degrees).

TABLE 1

| Symbol | Parameter Description | min | nom | max | unit |
|---|---|---|---|---|---|
| $Z_{21}$ | Axial coupling distance between external coil (loop 1) and implant coil (loop 2) | 5 | | 15 | mm |
| $a_{1, charge}$ | External coil radius for charging application | 10 | | 20 | mm |
| $a_{1, comm.}$ | External coil radius for communication application | 10 | | 15 | mm |
| $\rho_{21}$ | Radial displacement between loop 1 and loop 2 | 0 | | ±5 | mm |

TABLE 1-continued

| Symbol | Parameter Description | min | nom | max | unit |
|---|---|---|---|---|---|
| $\alpha_1$ | Inward tilt angle of loop 1 versus loop 2 | 0 | | ±10 | deg |
| $\beta_1$ | Sidewise tilt angle of loop 1 versus loop 2 | 0 | | ±5 | deg |

For the coils 315a, 365a of FIG. 4, coil shape was elliptically approximated, and the minor semi-axis b has a relationship to the major semi-axis a as shown in Equation 1.

$$b \geq a/\sqrt{2}, \text{ where } 10 \text{ mm} \leq \frac{a+b}{2} \geq 20 \text{ mm} \tag{1}$$

Figure 5A:
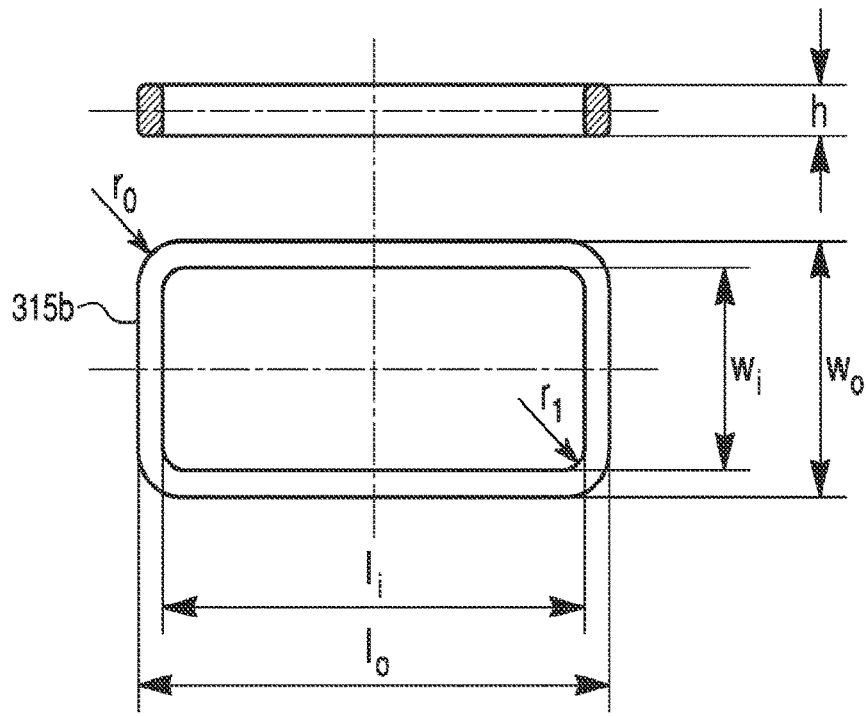
FIGS. 5A, 5B illustrate an example of a pair of coils in an RF recharging system in accordance with an embodiment of the present disclosure.
Figure 5B:
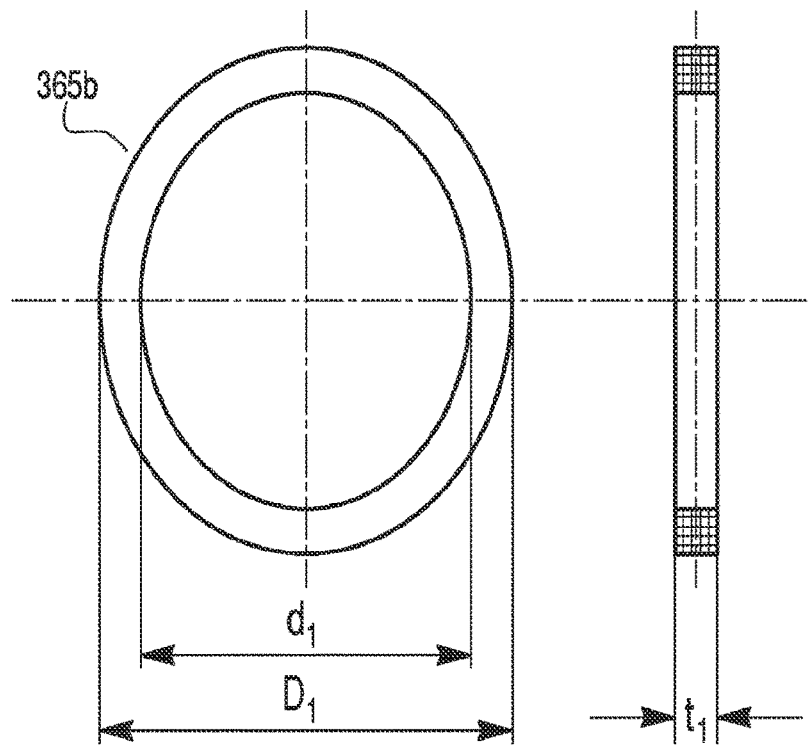

FIGS. 5A, 5B illustrate a pair of coils in an RF recharging system in accordance with an embodiment of the present disclosure. FIG. 5A illustrates a coil 315b (an example of the coil 315 of the recharging interface 305), and FIG. 5B illustrates a coil 365b (an example of a coil 365 of the recharger 355).

Table 2A provides dimensional parameters of the RF coil corresponding to FIG. 5A.

TABLE 2A

| Symbol | Parameter Description | min | nom | max | unit |
|---|---|---|---|---|---|
| h | IOI coil height | 0.20 | 0.3950 | 0.60 | mm |
| $l_i$ | IOI coil inner length | 2.66 | 5.3150 | 7.98 | mm |
| $l_o$ | IOI coil outer length | 2.9 | 5.7950 | 8.70 | mm |
| $m_{coil}$ | Total mass of the IOI coil | 12 | 25 | 37.5 | mg |
| $r_i$ | IOI coil inner radius | 0.13 | 0.2625 | 0.40 | mm |
| $r_o$ | IOI coil outer edge radius | 0.25 | 0.4975 | 0.75 | mm |
| $w_i$ | IOI coil inner width | 1.16 | 2.3150 | 3.48 | mm |
| $w_o$ | IOI coil outer width | 1.4 | 2.7950 | 4.2 | mm |

Table 2B provides electrical parameters of the RF coil corresponding to FIG. 5A as coupled to the RF coil of FIG. 5B, where measurements were taken on samples evaluated in a solution of 6.58 grams of NaCl per liter $H_2O$, at a frequency of $f_0$=13.56 MHz ('µH' refers to microhenries, 'Ω' refers to Ohms, 'MHz' refers to megahertz).

TABLE 2B

| Symbol | Parameter Description | min | nom | max | unit |
|---|---|---|---|---|---|
| $L_{22,air}$ | IOI coil inductance (15 turns) in air | 2.00 | 2.11 | 2.22 | µH |
| $L_{22,saline}$ | IOI coil inductance (15 turns) in saline | 2.07 | 2.18 | 2.29 | µH |
| $R_{22,DC}$ | IOI coil DC series resistance | 2.0 | 4.0 | 6.0 | Ω |
| $R_{22,air}$ | IOI coil series resistance at operating frequency in air | 7.15 | 7.53 | 7.91 | Ω |
| $R_{22,saline}$ | IOI coil series resistance at operating frequency in saline | 9.29 | 9.78 | 10.27 | Ω |
| $f_{SR,air}$ | IOI coil self-resonant frequency in air | 40 | 64.24 | — | MHz |
| $f_{SR,saline}$ | IOI coil self-resonant frequency in saline | 30 | 52.77 | — | MHz |

Table 2C provides parameters of the coil wire corresponding to the RF coil of FIG. 5A ('µm' refers to micrometers; 'V' refers to Volts).

TABLE 2C

| Symbol | Parameter Description | min | typ | max | unit |
|---|---|---|---|---|---|
| $d_{wire}$ | Diameter of conductive wire | 35 | 40 | 45 | µm |
| $t_{iso}$ | Isolation thickness | 3 | 5 | 7 | µm |
| $V_{BD}$ | Isolation breakdown voltage | 100 | | | V |

Figure 6:
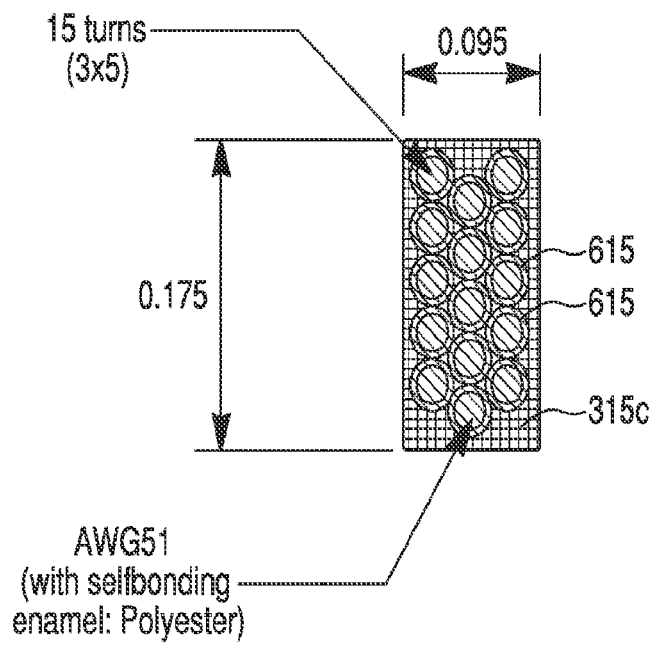
FIG. 6 illustrates an example of a coil in an RF recharging system in accordance with an embodiment of the present disclosure.

FIG. 6 illustrates a coil 315c (an example of the coil 315 of the recharging interface 305) in an RF recharging system in accordance with an embodiment of the present disclosure. In this embodiment, coil 315c includes multiple (shown as 15) interconnected small coils 615 providing an effective coil of fifteen turns. For example, one wire may be formed into fifteen coils, or multiple coils may be connected to form coil 315c. The coils 615 are formed of magnet wire, in which AWG51 wire (such as a copper AWG51 wire) is covered with a polyester and further covered with a self-bonding enamel. The dimensions of the coil 315c (with fifteen coils 615) is 0.175 mm by 0.095 mm.

Figure 7:
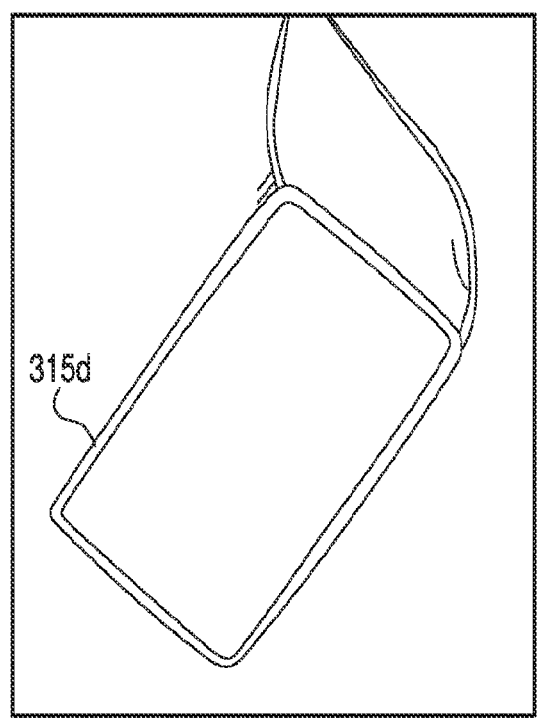
FIG. 7 illustrates an example of a coil in an RF recharging system in accordance with an embodiment of the present disclosure.

FIG. 7 illustrates a coil 315d (an example of the coil 315 of the recharging interface 305) in an RF recharging system in accordance with an embodiment of the present disclosure. In this embodiment, the overall dimensions of the coil 315d are similar to the overall dimensions of the coil 315c of FIG. 6, but the coil 315d is formed as a single coil shape instead of the fifteen coil shapes of the coil 315c. The coil 315d may be, for example, magnet wire such as described above.

In one or more embodiments, one or both of the coil 315c (FIG. 6) or the coil 315d (FIG. 7) is in a hermetically sealed non-permeable enclosure, such as hermetically sealed within glass. In such embodiments, the coil 315c or 315d is connected to wires or vias that extend through the enclosure for connection to the circuitry 310 (FIG. 3A).

In one or more embodiments, the coil 315 (FIG. 3) is formed as a thin film embedded in a substrate.

In one or more embodiments, the circuitry 310 and the coil 315 of the recharging interface 305 of FIG. 3A forms, or includes, a resonant circuit for efficient energy transfer. The term highly resonant in the present disclosure indicates a resonant circuit with a narrow-band resonant frequency, such that the resonant circuit is very responsive to frequencies at a resonant frequency, and slightly responsive at frequencies outside of a narrow band of frequencies around the resonant frequency. For example, a resonant frequency band may encompass frequencies that are within about ±1%, ±2%, ±3%, ±4%, or ±5%, of the resonant frequency.

Figure 8:
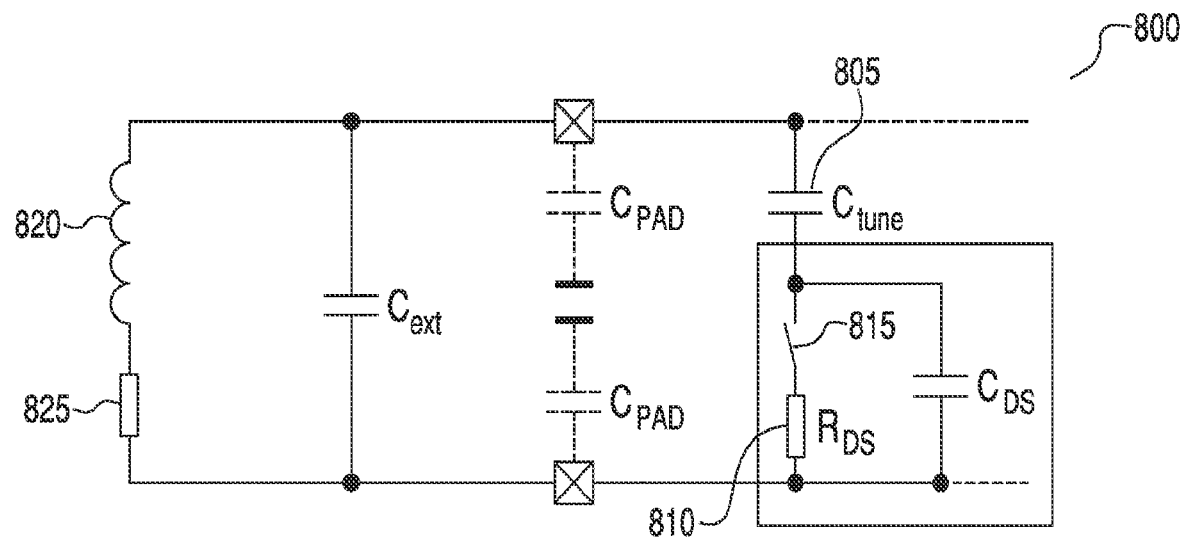
FIG. 8 illustrates an example of a circuit diagram representing a highly resonant circuit in a recharging interface in accordance with an embodiment of the present disclosure.

FIG. 8 illustrates an example of a circuit diagram representing a highly resonant circuit 800 in the recharging interface 305. The circuit 800 includes a tuning capacitor 805 with a tuning resistor 810 added when a switch 815 is closed. By closing the switch 815, the impedance of the circuit 800 changes, so that a resonance frequency of the circuit 800 may be changed, such as for improved matching to a charging frequency of the recharger 355, or to limit a recharging rate by moving the resonant frequency of the circuit 800 away from the charging frequency of the recharger 355, or to avoid interfering on a particular frequency band. In the circuit 800, the coil 315 of the recharging interface 305 is represented by an inductor 820 and a resistor 825.

Figure 9:
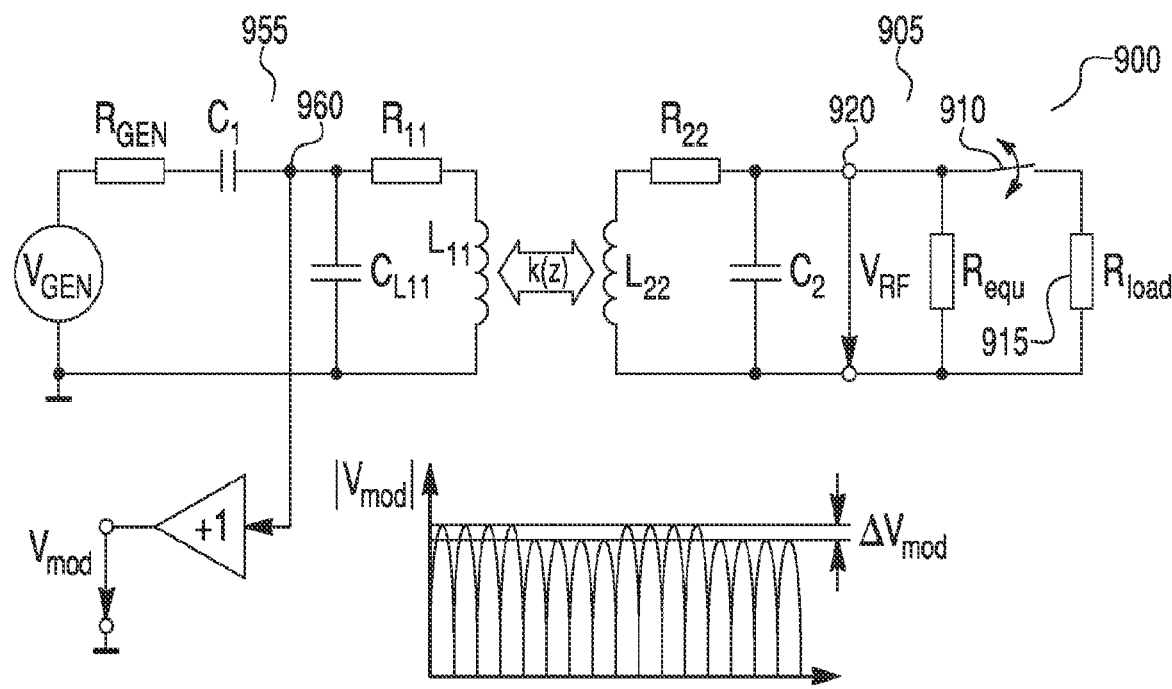
FIG. 9 illustrates an example of a circuit diagram representing a highly resonant circuit in an RF recharging system in accordance with an embodiment of the present disclosure.

FIG. 9 illustrates an example of a circuit diagram representing an RF recharging system 900 including a recharging interface 905 coupled to a recharger 955. The recharging interface 905 is highly resonant. The recharger 955 may also be highly resonant. The recharging interface 905 includes a switch 910 that, when closed, adds a load, represented by a resister 915 in parallel to the circuit. The load, for example, is an energy storage component (e.g., the energy storage component 320 of FIG. 3). When the load is switched in, the recharger 955 may detect a decrease in the voltage at a node 960, and correspondingly increase the voltage at the node 960 by an amount ΔVmod.

In one or more embodiments, as discussed with respect to FIG. 2, recharging interface 905 may also be a communication interface. In such embodiments, the resistor 915 is a modulation resistor for implementing a communication protocol. For example, when the switch 910 is closed to add the resistor 915 in parallel, the voltage level (or a change in the voltage level) at the node 960 of the recharger 955 may indicate a logic zero ('0'), and when the switch 910 is opened such that the resistor 915 is no longer in parallel, the voltage level (or a change in the voltage level) at the node 960 may indicate a logic one ('1'). Thus, the controller 120 (FIG. 2) associated with the recharging interface 905 can provide a sequence of ones and zeros to the recharger 955 by way of causing the switch 910 to open or close (or vice versa). Conversely, the recharger 955 can switch the modulation voltage in and out, and the voltage levels (or changes in the voltage levels) is measurable at the recharging interface at node 920, such that the controller 120 can detect ones and zeros by the voltage changes or levels at node 920.

Figure 10:
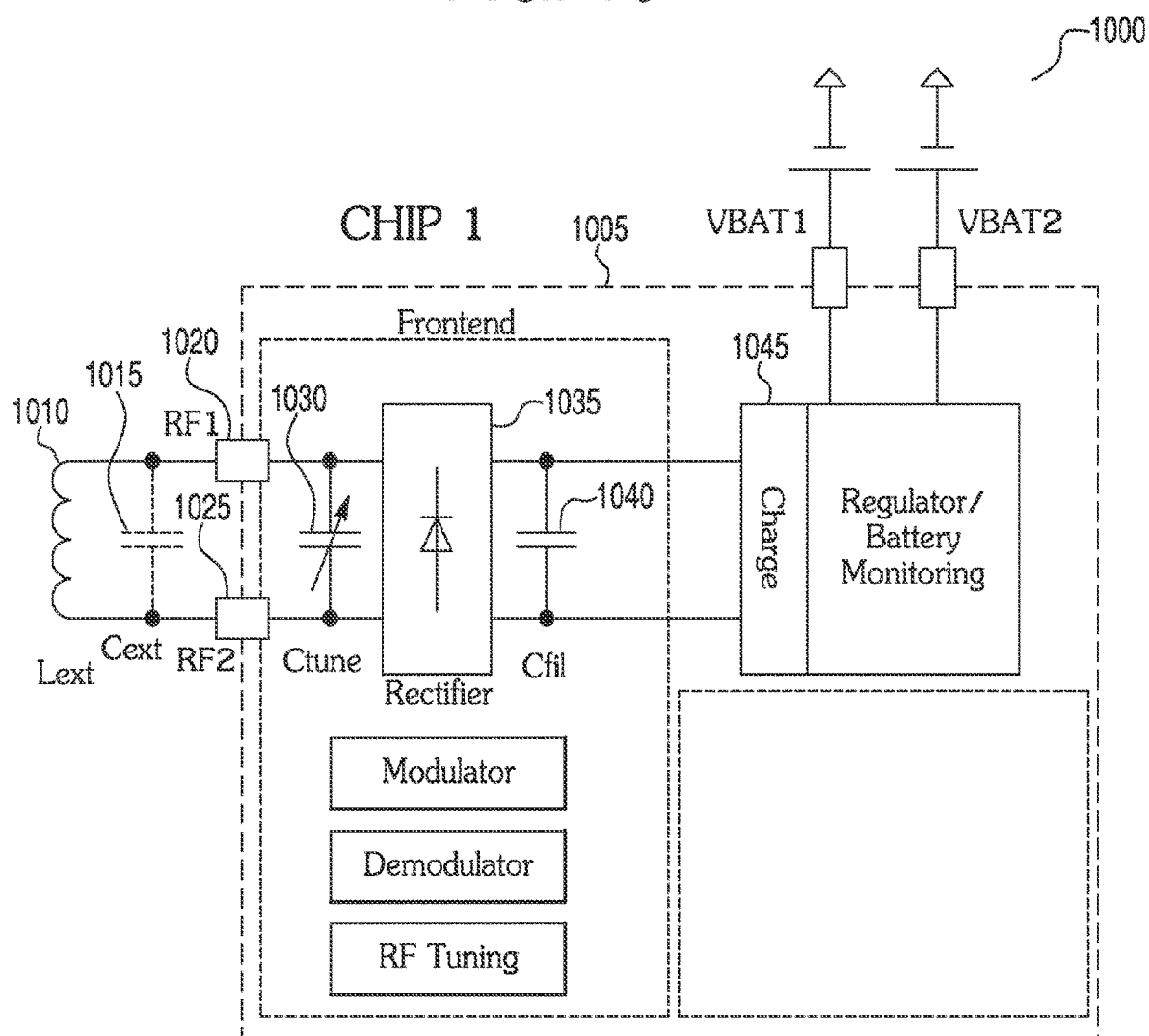
FIG. 10 illustrates a recharging interface implemented as an integrated circuit (IC) and an external coil in accordance with an embodiment of the present disclosure.

FIG. 10 illustrates a recharging interface 1000 implemented as an IC 1005, an external coil 1010, and an optional external capacitor 1015. The coil 1010 is connected to the IC 1005 at a node 1020 ('RF1') and node 1025 ('RF2'). A tunable capacitor 1030 is part of a resonant circuit of the recharging interface 1000. Energy is received at the coil 1010, and the voltage across the nodes 1020, 1025 is rectified by a rectifier circuit 1035. The rectified voltage is provided to a capacitor 1040, which is charged by energy received at the coil 1010. Energy in capacitor 1040 is used to recharge an energy storage device 1045 during an energy transfer.

Figure 11:
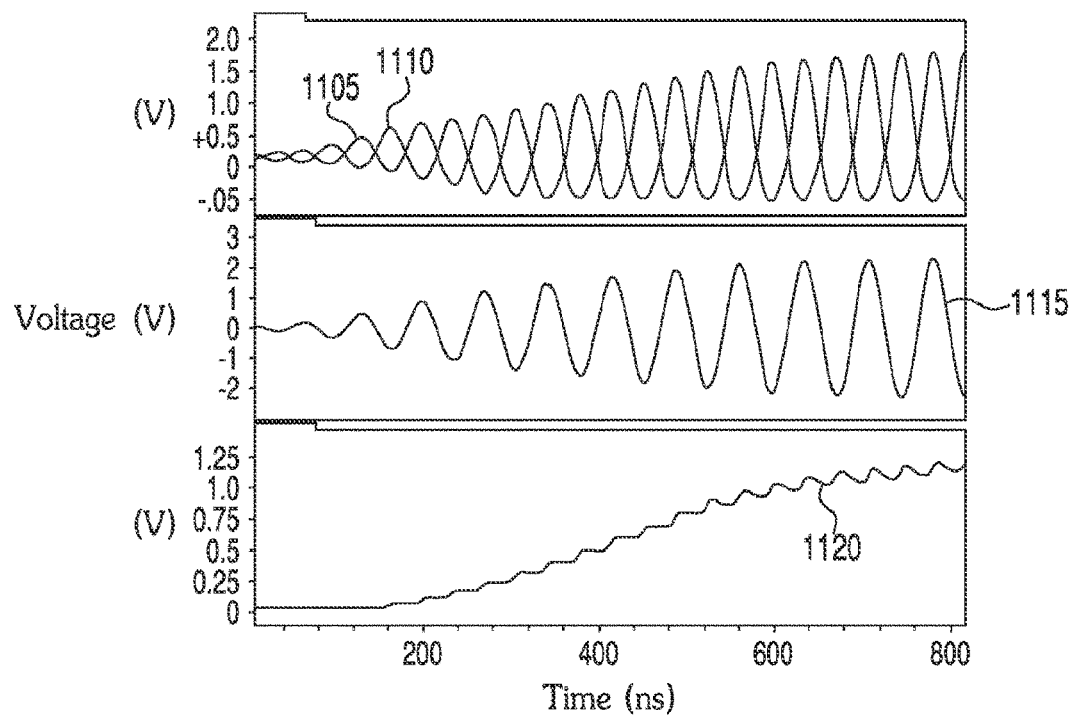
FIG. 11 presents plots of results of a simulation of using an RF link for recharging in accordance with an embodiment of the present disclosure.

FIG. 11 presents plots of results of a simulation of using an RF link for recharging, where the simulation includes a simulation of the recharging interface 1000 of FIG. 10 at a recharging frequency of 13.6 MHz. Traces 1105, 1110 represent the real and imaginary components of a voltage appearing across nodes 1020, 1025 (FIG. 10). Trace 1115 represents a voltage across the coil 1010, and trace 1120 represents a voltage across the capacitor 1040 during an energy transfer. As an energy transfer begins, the coil 1010 voltage begins to oscillate (trace 1115), and correspondingly, the voltages across the nodes 1020, 1025 begin to oscillate (traces 1105, 1110). An efficiency of the recharging interface is indicated by the voltage across the nodes 1020, 1025 as shown in traces 1105, 1110 versus the coil voltage of trace 1115. Soon after the coil voltage begins to oscillate (less than 220 nanoseconds (ns) in this simulation), the voltage across the capacitor 1040 begins to increase. The energy stored in the capacitor 1040 is provided to the energy storage device 1045 during and after the energy transfer through the coil 1010.

Figure 12:
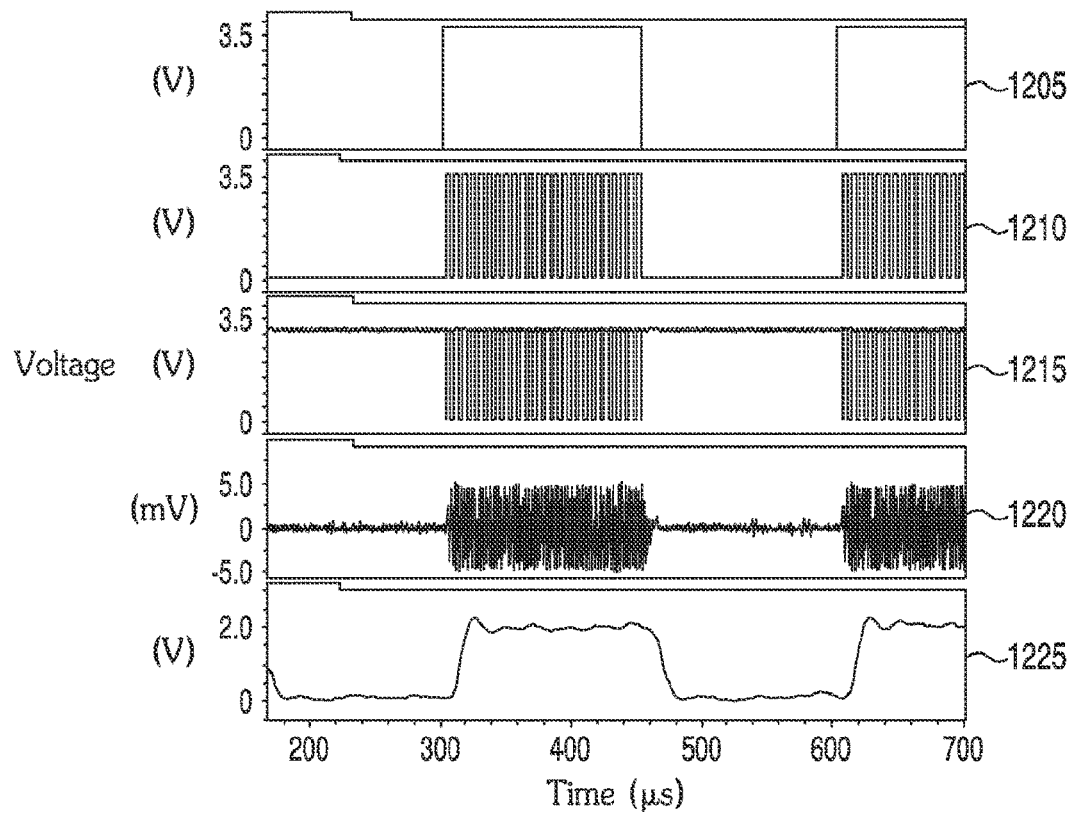
FIG. 12 presents plots of results of a simulation of using an RF link for communication in accordance with an embodiment of the present disclosure.

FIG. 12 presents plots 1205, 1210, 1215, 1220, 1225 which indicate results of a simulation of using the RF link for communication, where the simulation includes a simulation of the recharging interface 1000 of FIG. 10. For demonstration purposes, the communication is shown as a square wave at a frequency of approximately 3.3 kHz on a 13.6 MHz carrier frequency. The plot 1205 shows a square wave, the plot 1210 shows the square wave modulated on the 13.6 MHz carrier frequency, and the plot 1215 shows the modulated square wave as received at the recharging interface 1000. The plot 1220 indicates a filtered version of the received modulated square wave, which is further filtered to extract the square wave shown in the plot 1225 from the modulated signal. Comparing the plots 1205 to 1225, it can be seen that the square wave is interpreted correctly by the recharging interface 1000. Further, as the communication is being sent, the carrier frequency may be used to concurrently charge the power supply.

Figure 13:
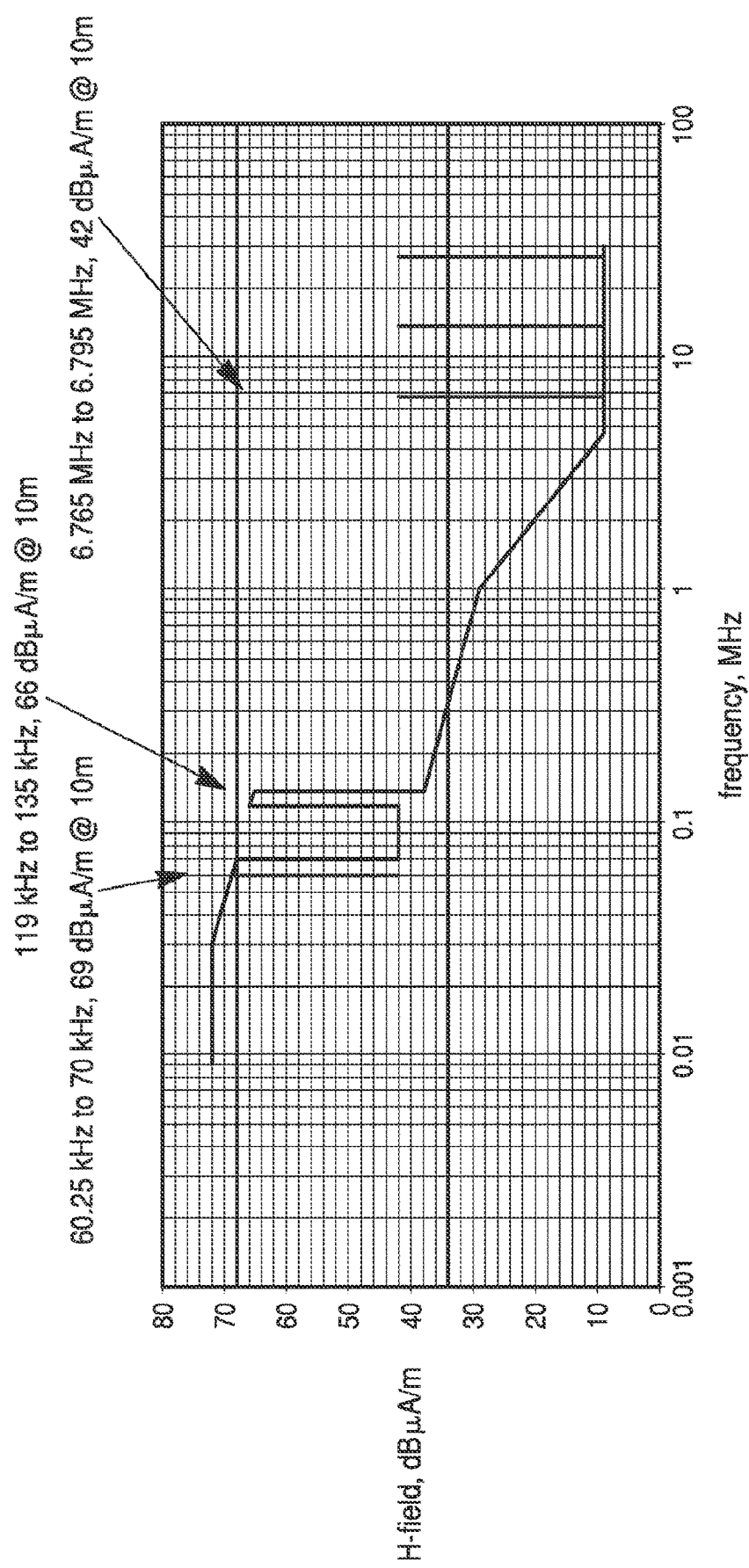
FIG. 13 is a frequency map showing permitted load levels as a function of frequency.

FIG. 13 is a frequency map generally showing load levels as a function of frequency, as permitted according to various regulations. Some example frequency bands are highlighted by way of example. Regulatory restrictions on implants arise out of health effects, based on absorption of electromagnetic radiation by the human body as a function of frequency. This is important when selecting the frequency bandwidth to be used for wireless transfer of energy through a human body to an implant. There is a spike in the map of FIG. 13 at about 13.6 MHz, where there is a narrow frequency band permitted to be used for implants. As shown with respect to FIGS. 11 and 12, both recharging and communication at 13.6 MHz are made possible for an IOI through the techniques described in this disclosure.

In one or more embodiments, rather than using RF for recharging and communication, another type of electromagnetic energy is used. For example, visible light, infrared (IR) or near-IR (NIR) light, or microwave radiation energy is used for recharging and communication. In one or more embodiments, visible light energy with a wavelength of 400 nanometers (nm) to 750 nm is used for recharging and communication. In one or more embodiments, infrared (or near infrared) light energy with a wavelength of 0.8 μm-1.3 μm is used for recharging and communication. In one or more embodiments, microwave radiation energy with a frequency of 1 MHz-900 MHz is used for recharging and communication.

Advantages of using light energy include the avoidance of electromagnetic interference caused by the alternating current (AC) of an RF transmission, as a light source is direct current (DC). Additionally, there are no (or few) bandwidth and power restrictions on light, versus many RF band or power restrictions. Other advantages include that energy can be harvested from ambient light sources; a light source may be very small, such a 1.8 mm×2.5 mm die that can produce 10 microwatts (μW) of power in the daylight; and fewer components may be used, as resonance is not a factor and no resonance capacitors are needed. Further, a light interface is less dependent on alignment, rotation and distance changes than are coils. For example, a misalignment of up to 2 centimeters (cm) can be tolerated with a light interface at a 2 cm distance and up to 45° rotation with little loss of power, and power in a light interface falls as 1/x with distance, versus $1/x^3$ for an RF interface.

It has been found that NIR light penetrates through skin tissue with low absorption (approximately a 10% absorption coefficient). It has further been found that NIR and IR penetration into the subcutaneous layer of the skin (e.g., greater than 3 mm) with little loss is possible. Experimental results indicate that a 730 nm NIR light can penetrate through an index finger approximately 10 mm thick, with 50% loss of power. It is thus expected that NIR or IR light at low power may be used for penetration through the iris (approximately 1 mm) to communicate with and recharge an IOI. It is likely that penetration may depend somewhat on eye color.

In one or more embodiments, the recharging interface 115 (FIG. 1 or FIG. 2) includes a photovoltaic (PV) cell. An example of a PV cell is an IXYS Corporation PV cell, part number CPC1822, The CPC1822 includes a 1.8 mm×2.5 mm die, provides an output of 17 µW (4.2 volts (V) at 4.2 microamps (µA)) in direct sunlight, and 0.9 µW (3 V at 0.3 µA) in ambient daylight, and has approximately a 90% relative efficiency at a 45 degree incidence angle.

In one or more embodiments, the recharger 150 (FIG. 1 or FIG. 2) includes an IR emitter. An example of an IR emitter is an Everlight Electronics IR emitter in a surface mount technology (SMT) package that emits light at 730 nm and has up to +/−60 degree spectral distribution, which allows for misalignment. The Everlight IR emitter comes in different versions, such as with a power output of 170 milliwatts (mW) or 1 Watt (W). The 170 mW version has a package size of 3.2×2.4 mm, induces 4 V at 4 µA (16 µW) in a CPC1822 PV cell at a distance of 2 cm with approximately 100 mW, and induces 2.8 V at 2.8 µA (8 µW) in a CPC1822 PV cell at a distance of 4 cm with approximately 100 mW.

Figure 14:
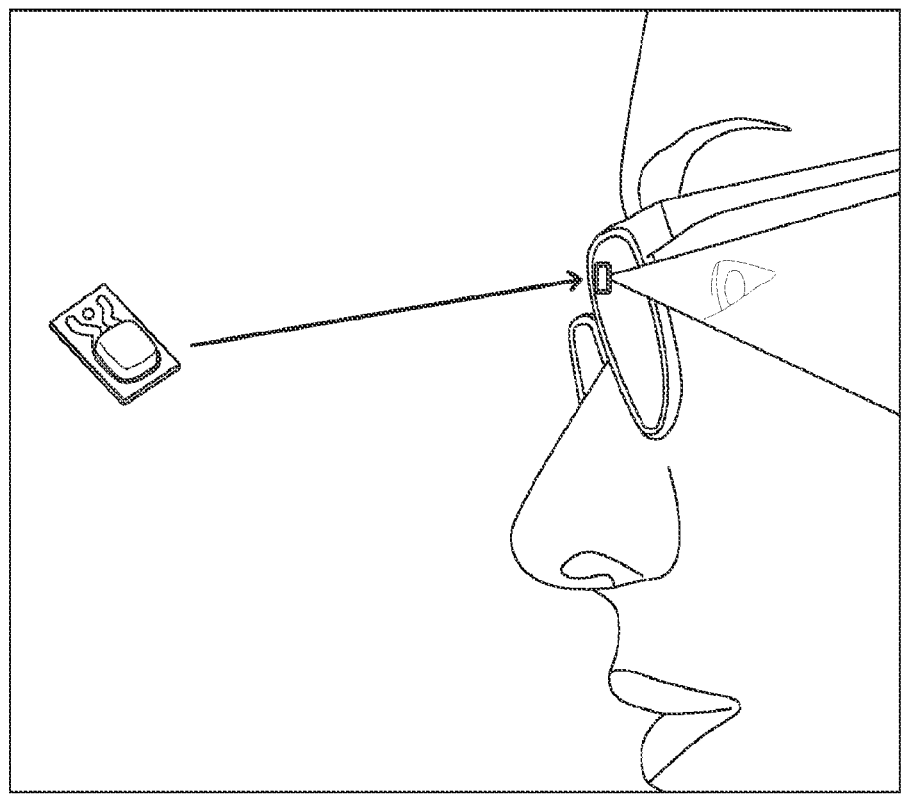
FIG. 14 illustrates an example of placement of a recharger in a pair of glasses in accordance with an embodiment of the present disclosure.

Whether it is a light interface or an RF interface, the recharger 150 (FIG. 1 or FIG. 2) may be embedded into a pair of glasses (see, e.g., FIG. 14), to be inconspicuous, or at the front of a headphone, in a cap or headband or other wearable item, or in a computing device. Multiple rechargers 150 may be embedded in or attached to objects around a building, so that a person with a rechargeable IOI according to this disclosure does not have to carry around a separate recharger 150 as they move around the building. For example, if the recharger 150 is in a mobile phone, each time the person looks at the mobile phone, an IR emitter or RF emitter could partially or completely recharge the IOI. For another example, the RF emitter could partially or completely recharge the IOI while the person is using the mobile phone as a telephone (with the speaker at the ear).

Also, as described above, repeaters may be positioned around a room or building to provide extended range of the person.

In one or more embodiments, in addition to receiving energy transfer (and/or communication) through the recharging interface 115 (FIG. 1 or FIG. 2), the IOI further is able to transfer energy (and/or communicate) through the recharging interface 115 to another device. For example, if a person has two IOIs, one in each eye, the recharging interfaces 115 of the two IOIs may be positioned towards the nose and in such a manner as to have good alignment when the eyes are focused in a particular direction. Thus, while reading or watching television or the like, one IOI may act as a recharger 150 for the other. Additionally or alternatively, one IOI may communicate with the other IOI over the recharging interfaces 115, or other communication interface, such as to control focusing in synchrony between the two IOIs.

The recharging described in this disclosure is applicable to many types of IOIs.

For example, in one embodiment, the IOI includes an electro-active optical cell, with a diffractive or refractive optic in contact with a liquid crystal whose refractive index can be modulated by application of a voltage. Such liquid crystal may be, for example, nematic or cholesteric. The electro-active cell may be dynamic (e.g., adjustable over a range) or switchable between states (e.g., two states, such as to add optical power for near vision). The controller 120 (FIGS. 1 and 2) controls the dynamic or state adjustment through actuators. The sensor 125 detects a physiological response that occurs when a person tries to change focus and experiences an accommodative impulse. An example of a sensor 125 that detects a physiological response is a photosensor. One or more photosensors are positioned at points (preferably several points) on the anterior surface of a lens in the IOI. Signals from the photosensors are filtered and interpreted by the controller 120, to determine when changes in signal amplitude represent pupillary constriction caused by an accommodative impulse.

In one or more embodiments, the controller 120 monitors a charge status of the power supply 105, and if a specified level is reached (e.g., a discharge threshold), the controller 120 initiates power-saving maneuvers such as not activating focal adjustment. Additionally, the controller 120 may send a communication periodically through the communication interface 135 or the recharging interface 115 to notify an external device to begin transferring energy, or that an energy transfer should be initiated.

In one or more embodiments, the controller 120 monitors for a communication from the recharger 150, such that when the recharger 150 is in proximity, an energy transfer may be performed.

In one embodiment, the controller 120 is an ASIC, specifically designed for the IOI, to reduce a size of the IOI. The ASIC may include portions of one or more of the communication interface 135 and the recharging interface 115.

Thus has been described an IOI system in which a size of an IOI is significantly reduced by providing interfaces and techniques for frequent recharging of the IOI. The system provides for usable energy transfer efficiencies despite the very small radius of the receiver coil compatible with space constraints in an intraocular implant.

As used herein, the terms "approximately," "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations is not a limitation of the disclosure.

What is claimed is:

1. An intraocular implant system, comprising:
   a) an electromagnetic charging interface configured to wirelessly receive electrical energy from an external wireless recharger, the electromagnetic charging interface having a resonant frequency and comprising a switch disposed in series with a tuning capacitor and a tuning resistor; and
   b) an intraocular implant (IOI), comprising:

i) a wireless communication interface configured to wirelessly communicate with an external remote-control device;
   ii) a lens structure with variable optical power;
   iii) a sensor configured to detect a first optical accommodation information signal that is received by the wireless communication interface;
   iv) a rechargeable power storage device; and
   v) a controller configured to:
      A) control the variable optical power of the lens structure of the IOI based on the first optical accommodation information signal detected by the sensor;
      B) control the electromagnetic charging interface to charge the rechargeable power storage device with electrical energy received by the electromagnetic charging interface from the external wireless recharger;
      C) provide power from the rechargeable power storage device for operation of the IOI; and
      D) wirelessly transmit data regarding the IOI to the remote-control device and receive instructions and updates for the IOI from the remote-control device through the wireless communication interface,
   c) wherein, when the switch of the electromagnetic charging interface is closed, the tuning resistor in series with the tuning capacitor are configured to perform at least one of:
      i) matching the resonant frequency of the electromagnetic charging interface with a charging frequency of an external wireless recharger;
      ii) moving the resonant frequency of the electromagnetic charging interface away from a charging frequency of the external wireless recharger to thereby limit a rate at which the rechargeable power storage device is charged by the external wireless recharger; and
      iii) adjusting the resonant frequency of the electromagnetic charging interface to prevent charging the rechargeable power storage device at a predefined resonant frequency.

2. The intraocular implant system of claim 1, wherein the variable optical power of the lens structure is a selection between at least a first predefined optical power and a second predefined optical power.

3. The intraocular implant system of claim 1, wherein the rechargeable power storage device is a super-capacitor.

4. The intraocular implant system of claim 1, wherein the electromagnetic charging interface serves as the wireless communication interface.

5. The intraocular implant system of claim 1, wherein the controller is reprogrammable through the wireless communication interface.

6. The intraocular implant system of claim 1, wherein the IOI is a first IOI, and the controller is further configured to control a second IOI.

7. The intraocular implant system of claim 6, wherein the controller is configured to control the variable optical power of a second lens structure of the second IOI based on a second optical accommodation information signal detected by the sensor.

8. The intraocular implant system of claim 1, wherein the IOI is a first IOI, and the controller is further configured to provide power from the rechargeable power storage device to a second IOI.

9. The intraocular implant system of claim 1, wherein the electromagnetic charging interface includes a coil.

10. The intraocular implant system of claim 1, wherein the resonant frequency of the electromagnetic charging interface is about 13.6 MHz.

11. The intraocular implant system of claim 1, wherein, when the switch of the electromagnetic charging interface is closed, an energy storage device is added in parallel with the electromagnetic charging interface, and wherein the electromagnetic charging interface is then configured to detect a decrease in voltage at a node and correspondingly increase the voltage at the node by an amount equal to the detected decrease in voltage.

12. The intraocular implant system of claim 1, wherein the controller is further configured to wirelessly transmit data regarding a second IOI to the remote-control device and receive instructions and updates for the second IOI from the remote-control device through the wireless communication interface.

13. The intraocular implant system of claim 1, wherein, when the switch of the electromagnetic charging interface is closed, the series connected tuning resistor and tuning capacitor are configured to prevent charging the rechargeable power storage device at a predefined resonant frequency band.

14. The intraocular implant system of claim 1, wherein, when the switch of the electromagnetic charging interface is closed, the series connected tuning resistor and tuning capacitor are configured to:
   a) match the resonant frequency of the electromagnetic charging interface with a charging frequency of an external wireless charger;
   b) move the resonant frequency of the electromagnetic charging interface away from a charging frequency of the external wireless charger to thereby limit a rate at which the rechargeable power storage device is charged by the wireless charger; and
   c) adjust the resonant frequency of the electromagnetic charging interface to prevent charging the rechargeable power storage device at a predefined resonant frequency.

15. An intraocular implant system, comprising:
a) a radiofrequency (RF) charging interface configured to the wirelessly receive electrical energy from an external wireless recharger, wherein the RF charging interface comprises a resonant circuit having a coil with a resonant frequency and a switch disposed in series with a tuning capacitor and a tuning resistor; and
b) an intraocular implant (IOI), comprising:
   i) a wireless communication interface configured to wirelessly communicate with an external remote-control device;
   ii) a lens structure with variable optical power;
   iii) a sensor configured to detect optical accommodation information that is received by the wireless communication interface;
   iv) a rechargeable power storage device; and
   v) a controller configured to:
      A) control the variable optical power of the lens structure of the IOI based on optical accommodation information detected by the sensor;
      B) control the RF charging interface to charge the rechargeable power storage device with electrical energy received by the RF charging interface from the external wireless recharger;
      C) provide power from the rechargeable power storage device for operation of the IOI; and
      D) wirelessly transmit data regarding the IOI to remote-control device and receive instructions and updates for the IOI from the remote-control device through the wireless communication interface, c) wherein, when the switch of the RF charging interface is closed, the series connected tuning resistor and tuning capacitor are configured to perform at least one of:
   i) matching the resonant frequency of the RF charging interface with a charging frequency of the external wireless recharger;
   ii) moving the resonant frequency of the RF charging interface away from a charging frequency of the external wireless recharger to thereby limit a rate at which the rechargeable power storage device is charged by the external wireless recharger; and
   iii) adjusting the resonant frequency of the RE charging interface to prevent charging the rechargeable power storage device at a predefined resonant frequency.

16. The intraocular implant system of claim 15, wherein the energy storage device is one of a super-capacitor or an ultra-capacitor.

17. The intraocular implant system of claim 15, wherein the coil of the RF charging interface has a weight in air not exceeding 50 milligrams.

18. The intraocular implant system of claim 15, wherein the coil of the RF charging interface has a minimum length of wiring not less than 15 mm.

19. The intraocular implant system of claim 15, wherein the coil of the RF charging interface is formed of a thin film embedded in a substrate.

20. The intraocular implant system of claim 15, wherein the resonant frequency of the radiofrequency (RF) interface is about 13.6 MHz.

21. An intraocular implant system, comprising:
   a) an electromagnetic charging interface configured to wirelessly receive electrical energy from an external wireless recharger, the electromagnetic charging interface having a resonant frequency and comprising a switch disposed in series with a tuning capacitor and a tuning resistor; and
   b) an intraocular implant (IOI), comprising:
      i) a wireless communication interface configured to wirelessly communicate with an external remote-control device;
      ii) a lens structure with variable optical power;
      iii) a sensor configured to detect an optical accommodation information signal that is received by the wireless communication interface;
      iv) a rechargeable power storage device; and
      v) a controller configured to:
         A) control the variable optical power of the lens structure of the IOI based on the optical accommodation information signal detected by the sensor;
         B) control the electromagnetic charging interface to charge the rechargeable power storage device with the wirelessly received electrical energy received by the electromagnetic charging interface from the external wireless recharger;
         C) provide power from the rechargeable power storage device for operation of the IOI; and
         D) wirelessly transmit data regarding the IOI to the remote-control device and receive instructions and updates for the IOI from the remote-control device through the wireless communication interface, c) wherein, when the switch of the electromagnetic charging interface is closed, the series connected tuning resistor and tuning capacitor are selectively configured to perform each of:
   i) matching the resonant frequency of the electromagnetic charging interface with a charging frequency of the external wireless recharger;
   ii) moving the resonant frequency of the electromagnetic charging interface away from the charging frequency of the external wireless recharger to thereby limit a rate at which the rechargeable power storage device is charged by the external wireless recharger; and
   iii) adjusting the resonant frequency of the electromagnetic charging interface to prevent charging the rechargeable power storage device at a predefined resonant frequency.

22. The intraocular implant system of claim 21, wherein the resonant frequency of the electromagnetic charging interface is about 13.6 MHz.

* * * * *